(12) United States Patent
Voytik-Harbin et al.

(10) Patent No.: US 7,147,871 B2
(45) Date of Patent: Dec. 12, 2006

(54) SUBMUCOSA GEL COMPOSITIONS

(75) Inventors: Sherry L. Voytik-Harbin, Zionsville, IN (US); Andrew O. Brightman, West Lafayette, IN (US); Ryan M. Meixner, Minnetonka, MN (US); Beverly Z. Waisner, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/233,888

(22) Filed: Sep. 3, 2002

(65) Prior Publication Data
US 2003/0012823 A1 Jan. 16, 2003

Related U.S. Application Data

(63) Continuation of application No. 09/911,144, filed on Jul. 23, 2001, now Pat. No. 6,444,229, and a continuation of application No. 09/622,244, filed as application No. PCT/US99/04352 on Feb. 26, 1999, now Pat. No. 6,264,992.

(60) Provisional application No. 60/076,690, filed on Feb. 27, 1998.

(51) Int. Cl.
*A61K 35/37* (2006.01)
*A61K 35/38* (2006.01)
*C12P 21/06* (2006.01)

(52) U.S. Cl. ............................... 424/551; 435/68.1
(58) Field of Classification Search ................ 424/422, 424/551; 422/551; 435/391, 455, 68.1; 514/44; 536/23.1
See application file for complete search history.

(56) References Cited

U.S. PATENT DOCUMENTS

| | | | |
|---|---|---|---|
| 4,829,000 A | 5/1989 | Kleinman et al. | |
| 4,902,508 A | 2/1990 | Badylak et al. | |
| 4,956,178 A | 9/1990 | Badylak et al. | |
| 5,275,826 A | 1/1994 | Badylak et al. | |
| 5,281,422 A | 1/1994 | Badylak et al. | |
| 5,516,533 A | 5/1996 | Badylak et al. | |
| 5,554,389 A | 9/1996 | Badylak et al. | |
| 5,641,518 A * | 6/1997 | Badylak et al. | 424/551 |
| 5,695,998 A | 12/1997 | Badylak et al. | |
| 5,753,267 A * | 5/1998 | Badylak et al. | 424/551 |
| 6,099,567 A | 8/2000 | Badylak et al. | |

FOREIGN PATENT DOCUMENTS

| | | |
|---|---|---|
| WO | WO 96/24661 | 8/1996 |
| WO | WO 98/25636 | 6/1998 |
| WO | WO 98/25964 | 6/1998 |

OTHER PUBLICATIONS

Sigma Cell Culture Catalog. 1992. pp. 246-247.*
Kleinman et al., "Basement Membrane Complexes with Biological Activity," *Biochemistry*, vol. 25, pp. 312-318 (1986).
Elsdale et al., "Collagen Substrata For Studies on Cell Behavior," *The Journal of Cell Biology*, vol. 54, pp. 626-637 (1972).
Bell et al., "Production of a tissue-like structure by contraction of collagen lattices by human fibroblasts of different proliferative potential *in vitro*," *Proc. Natl. Acad. Sci.*, vol. 76, No. 3., pp. 1274-1278 (1979).
Emerman et al., "Maintenance and Induction of Morphological Differentiation in Dissociated Mammary Epithelium on Floating Collagen Membranes," *InVitro*, vol. 13, No. 5, pp. 316-328 (1977).
Kleinman, et al., "Preparation of Collagen Substrates for Cell Attachment: Effect of Collagen Concentration and Phosphate Buffer," *Analytical Biochemistry*, vol. 94, pp. 308-312 (1979).
Bornstein, "Reconstituted Rat-Tail Collagen Used as Substrate for Tissue Cultures on Coverslips in Maximow Slides and Roller Tubes," *Lab. Investig.*, vol. 7., No. 2, pp. 134-137 (1958).
Voytik-Harbin et al., "Small Intestinal Submucosa: A Tissue-Derived Extracellular Matrix That Promotes Tissue Specific Growth and Differentiation of Cells *in Vitro*," *Tissue Engineering*, vol. 4, No. 2, pp. 157-174 (1998).
Voytik-Harbin et al., "Identification of Extractable Growth Factors From Small Intestinal Submucosa," *Journal of Cellular Biochemistry*, vol. 67: 478-491 (1997).

* cited by examiner

*Primary Examiner*—Ralph Gitomer
*Assistant Examiner*—Kailash C. Srivastava
(74) *Attorney, Agent, or Firm*—Barnes & Thornburg LLP

(57) ABSTRACT

A composition comprising enzymatically digested submucosa of a warm-blooded vertebrate and a method of making that composition is described. More particularly the submucosa is enzymatically digested and gelled to form a shape retaining gel matrix suitable for inducing cell proliferation and growth both in vivo and in vitro.

6 Claims, No Drawings

SUBMUCOSA GEL COMPOSITIONS

CROSS-REFERENCE TO RELATED APPLICATIONS

This application is a continuation application of U.S. patent application Ser. No. 09/911,144, filed on Jul. 23, 2001 now U.S. Pat. No. 6,444,229, which claims priority to U.S. patent application Ser. No. 09/622,244, filed on Aug. 15, 2000 now U.S. Pat. No. 6,264,992, which is a U.S. National Application of international application Ser. No. PCT/US99/04352, filed Feb. 26, 1999, which claims priority to U.S. Provisional Application Ser. No. 60/076,690, filed on Feb. 27, 1998.

FIELD OF THE INVENTION

The present invention relates to the preparation of submucosa-derived gel compositions and their use for inducing the proliferation and growth of cells in vivo and in vitro. More particularly, this invention is directed to an improved matrix comprising warm-blooded vertebrate submucosa that has been fluidized by enzymatic digestion and then gelled to form a shape retaining matrix. In one embodiment the matrix is used as an improved cell culture substrate to support the growth and tissue differentiation of eukaryotic cells in vitro. Alternatively, the compositions of the present invention can be implanted or injected into a host to induce cell growth and proliferation in vivo.

BACKGROUND OF THE INVENTION

Tissue culture allows the study in vitro of animal cell behavior in an investigator-controlled physicochemical environment. However, cellular morphology and metabolic activity of cultured cells are affected by the composition and architecture of the substrate on which they are grown. Presumably cultured cells function best (i.e. proliferate and/or perform their natural in vivo functions) when cultured on substrates that closely mimic their natural environment.

The interaction of cells with their extracellular matrix (ECM) in both in vivo and in vitro environments plays a crucial role in the organization, homeostasis, and function of all tissues and organs. Continuous communication between cells and the surrounding matrix environment orchestrates critical processes such as the acquisition and maintenance of differentiated phenotypes during embryogenesis, the development of form (morphogenesis), angiogenesis, wound healing, and even tumor metastasis. The cell and its ECM are said to exist in a state of "dynamic reciprocity". Both biochemical and biophysical signals from the ECM modulate fundamental cellular activities including adhesion, migration, proliferation, differential gene expression, and programmed cell death.

In turn, the cell can modify its ECM environment by modulating synthesis and degradation of specific matrix components. The realization of the significance of cell-ECM communication has led to a renewed interest in characterizing ECM constituents and the basic mechanisms of cell-ECM interaction.

Currently, studies conducted in vitro for analyzing cellular function are limited by the availability of cell growth substrates that present the appropriate physiological environment for proliferation and function/growth development of the cultured cells. To provide an in vitro cell culture environment which would more closely mimic cell-ECM interaction in vivo, purified ECM components such as collagen, fibronectin, laminin, glycosaminoglycans (e.g., hyaluronic acid, heparan sulfate) have been used to prepare artificial substrata for augmentation of cell adhesion, growth, and morphology. Three-dimensional (3D) culture matrices also have been fashioned from purified ECM components, specifically fibrin clots and collagen gels. Investigations with these matrices have demonstrated the importance of 3D architecture in the establishment of a tissue-like histology.

Complex scaffolds representing combinations of ECM components in a natural or processed form are commercially available. For example, Becton Dickinson currently offers two such products: Human Extracellular Matrix, and MATRIGEL® Basement Membrane Matrix. Human Extracellular Matrix is a chromatographically partially purified matrix extract derived from human placenta and comprises laminin, collagen IV, and heparin sulfate proteoglycan. (Kleinman, H K et al., U.S. Pat. No. 4,829,000 (1989).) MATRIGEL® is a soluble basement membrane extract of the Engelbreth-Holm-Swarm (EHS) tumor, gelled to form a reconstituted basement membrane. Both of these basement membrane extracellular matrix products require costly biochemical isolation, purification, and synthesis techniques and thus production costs are high.

Additional basement membrane matrices utilized as cell culture substrates include allogeneic and xenogeneic compositions prepared from lens capsule, liver, amnion, and chorioallantoic membranes. Although these substrata allow the study of cell growth and differentiation in a more physiologically relevant system, their use has been limited by availability and amenability to disinfection, sterilization, and manufacturing processes.

The present invention is directed to the preparation of a collagenous gel matrix derived from the interstitial extracellular matrix of warm-blooded vertebrate tissues. The predominant collagen types present such matrices are collagen I, III and V. The matrices for use in accordance with the present invention are derived from tissues comprising highly conserved collagens, glycoproteins, proteoglycans, and glycosaminoglycans in their natural configuration and natural concentration. One extracellular collagenous matrix for use in this invention is derived from submucosal tissue of a warm-blooded vertebrate.

Submucosal tissue harvested from warm-blooded vertebrates is a collagenous matrix that has shown great promise as a unique graft material for inducing the repair of damaged or diseased tissues in vivo, and for inducing the proliferation and differentiation of cell populations in vitro.

As a tissue graft, submucosal tissue undergoes remodeling and induces the growth of endogenous tissues upon implantation into a host. Numerous studies have shown that submucosal tissue is capable of inducing host tissue proliferation, remodeling and regeneration of tissue structures following implantation in a number of in vivo microenvironments, including lower urinary tract, body wall, tendon, ligament, bone, cardiovascular tissues and the central nervous system. It has been used successfully in vascular grafts, urinary bladder and hernia repair, replacement and repair of tendons and ligaments, and as a dermal graft. Upon implantation, cellular infiltration and a rapid neovascularization are observed and the submucosa extracellular matrix material is remodeled into host replacement tissue with site-specific structural and functional properties.

Vertebrate submucosa can be obtained from various sources, including intestinal tissue harvested from animals raised for meat production, including, for example, pigs, cattle and sheep or other warm-blooded vertebrates. The preparation and use of submucosa as a tissue graft composition is described in U.S. Pat. Nos. 4,902,508; 5,281,422; 5,275,826; 5,554,389 and other related U.S. patents. Submucosal tissue consists primarily of extracellular matrix material and is prepared by mechanically removing selected portions of the mucosa and the external muscle layers and then lysing resident cells with hypotonic washes. Preliminary biochemical analyses show that the composition of small intestinal submucosa is similar to that of other interstitial extracellular matrix structures, and consists of a complex array of collagen, proteoglycans, glycosaminoglycans, and glycoproteins. The major components commonly identified in extracellular matrix tissues similar to submucosal tissue include growth factors; the cell adhesion proteins, fibronectin, vitronectin, thrombospondin, and laminin; the structural components, collagen and elastin; and the proteoglycans, serglycin, versican, decorin, and perlecan.

Submucosa tissue can be used as a tissue graft construct, or as a cell culture substrate/supplement, in either its native solid form, as a fluidized comminuted form, or as an enzyme digested solubilized form. Furthermore, the solubilized forms of vertebrate submucosa can be gelled to form a semi-solid composition that can be implanted as a tissue graft construct or utilized as a cell culture substrate. As a tissue graft, the enzyme-digested, solubilized form can be injected or otherwise delivered to living tissues to augment, enhance or suppress the structure or function of said tissue. Furthermore, said enzyme-digested, solubilized form can be combined or modified with specific proteins, growth factors, drugs, plasmids, vectors, or other therapeutics agents for controlling the desired augmentation, enhancement or suppression of the recipient tissue function. Still further, said enzyme-digested, solubilized form can be combined with living primary or cultured cells prior to delivery to the living tissues, such combination providing further augmentation, enhancement of suppression of tissue structure or function. The submucosa gel form can also be used as a cell growth substrate, providing a relatively inexpensive cell culture growth substrate that promotes or induces growth and differentiation of cells cultured in vitro.

SUMMARY OF THE INVENTION

The present invention is directed to an improved vertebrate submucosa composition comprising a semi-solid translucent interstitial extracellular matrix formed from solubilized submucosa of a warm-blooded vertebrate, and a method of forming that composition. More particularly, the interstitial extracellular matrix comprises submucosa that has been enzymatically digested to form a submucosa hydrolysate, wherein the submucosa hydrolysate is fractionated and then gelled.

DETAILED DESCRIPTION OF THE PREFERRED EMBODIMENTS

The present invention is directed to compositions comprising vertebrate submucosa in gelled form and a method of making an improved submucosa gel. As used herein, a gel is a fluid having a viscosity of greater than about 100,000 cps at 25° C., and more typically having a viscosity of about 200,000 to about 350,000 cps at 25° C., such that the fluid is in a semi-solid form that only gradually yields to forces that change its form. Gelled forms of vertebrate submucosa can be prepared by increasing the viscosity of solubilized submucosa, and in one preferred embodiment the solubilized submucosa is gelled by inducing the self assembly of the polymer components of the submucosa. In accordance with one embodiment a submucosa gel is prepared by enzymatically treating vertebrate submucosa to produce a submucosa hydrolysate, wherein the submucosa hydrolysate is gelled by raising the pH to about 6.0 to about 7.4. The term "submucosa hydrolysate" as used herein refers to isolated warm-blooded vertebrate submucosa that has been enzymatically treated to reduce the molecular weight of at least some of the submucosa structural components and produce a composition comprising solubilized components of the isolated submucosa. The submucosa hydrolysate may include insoluble and/or nonhydrolyzed components of the isolated submucosa as well as solubilized components.

In accordance with one embodiment of the present invention, an improved method of forming a gel composition comprising vertebrate submucosa is described. The method produces a translucent, sliceable, shape retaining gel, comprising warm-blooded vertebrate submucosa that has been hydrolyzed and fractionated. The term "shape retaining gel" is defined herein to refer to a gel that holds its three dimensional molded shape (i.e. no significant change in the height, length or width) in a hydrated environment for at least one hour at 20° C. after removal from the mold and placement on a flat surface without any other support. The method of forming the shape retaining gel of the present invention comprises the steps of enzymatically treating warm-blooded vertebrate submucosa to produce a hydrolysate of vertebrate submucosa having multiple hydrolyzed submucosa components, fractionating the hydrolysate to remove at least a portion of the hydrolysate components and gelling the fractionated hydrolysate. Advantageously, the present method enables the formation of a translucent, shape retaining gel from a complex extracellular matrix without purification of the matrix collagen compounds. Accordingly, the submucosa gel retains many of the original components of the solid delaminated vertebrate submucosa. Furthermore, the gel compositions are particularly well suited for use as cell culture substrates since their relative transparency allows for direct visualization of cells growing on and/or within the submucosa gel matrix.

Submucosal tissue used as the source and starting material for the gel compositions of the present invention comprises submucosa isolated from warm-blooded intestinal tissue as well as other tissue sources such as the alimentary, respiratory, urinary or genital tracts of warm-blooded vertebrates. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in PCT published application No. WO98/25636, published on Jun. 18, 1998, titled STOMACH SUBMUCOSA DERIVED TISSUE GRAFT, the disclosure of which is expressly incorporated herein by reference. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100–200 micrometers, and consists primarily (greater than 98%) of acellular, eosinophilic staining (H&E stain) extracellular matrix material.

Preferred submucosal tissues for use as a source of gelled compositions of the present invention include intestinal submucosa, stomach submucosa, urinary bladder submucosa, and uterine submucosa. Intestinal submucosal tissue is one preferred starting material, and more particularly the tunica submucosa delaminated from both the tunica muscularis and at least the luminal portion of the tunica mucosa of warm-blooded vertebrate intestine. In one embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The isolated vertebrate submucosa is typically rinsed extensively with a hypotonic solution to lyse any cells still associated with the submucosal matrix and to eliminate cell degradation products. To produce the solubilized forms of submucosa utilized to form the gel compositions of the present invention, the submucosa is treated with a disruptive agent that solubilizes the submucosa without substantial destruction of the collagen components of the submucosa. In one embodiment the submucosa is treated with one or more enzymes for a predetermined length of time sufficient to hydrolyze at least a portion of the submucosa structural components and produce a submucosa hydrolysate. Typically the submucosa is comminuted before enzymatic digestion of the submucosa by tearing, cutting, grinding, or shearing the harvested submucosal tissue. More particularly, the submucosa can be comminuted by shearing in a high speed blender, or by grinding the submucosa in a frozen or freeze-dried state, and then lyophilizing the material to produce a powder having particles ranging in size from about 0.1 to about 1.0 $mm^2$. The submucosa powder can thereafter be hydrated with water or buffered saline to form a submucosal fluid of liquid or paste-like consistency. In one preferred embodiment the submucosal tissue is comminuted by freezing and pulverizing the submucosa under liquid nitrogen in an industrial blender. The preparation of fluidized forms of submucosa tissue is described in U.S. Pat. No. 5,275,826, the disclosure of which is expressly incorporated herein by reference.

Enzymatic digestion of the submucosa is conducted under conditions that retain the ability of the endogenous submucosa collagen fibers to self assemble. The concentration of the enzyme used is adjusted based on the specific enzyme used, the amount of submucosa to be digested, the predetermined time of digestion, the temperature of the reaction, and the desired properties of the final product. In one embodiment about 0.1% to about 0.2% of enzyme (pepsin, for example) is added and the digestion is conducted at 4° C. for 72 hours. However the digestion can be conducted at any temperature ranging from 4–37° C. and the digestion times can be adjusted accordingly from 2–180 hours. In general, the ratio of the concentration of submucosa (hydrated) to total enzyme ranges from about 25 to about 125 and more typically the ratio is about 50, and the digestion is conducted at 4° C. for 24–72 hours. The composition of the gel produced from the submucosa hydrolysate will vary, at least in the proportion of their components if not also in the gel contents, depending on the length of digestion and digestive agent used.

The enzymes or other disruptive agents used to solubilize the submucosa should be removed or inactivated before or during the gelling process so as not to compromise gel formation or subsequent gel stability. Also, any disruptive agent, particularly enzymes, that remain present and active during storage of the tissue will change the composition and potentially the gelling characteristics of the solution. Enzymes, such as pepsin, can be inactivated with protease inhibitors, a shift to neutral pH, a drop in temperature below 0° C., heat inactivation or through the removal of the enzyme by fractionation. A combination of these methods can be utilized to stop digestion of the submucosa at a predetermined endpoint, for example the submucosa can be immediately frozen and later fractionated to limit the digestion of the submucosa.

The submucosa is enzymatically digested for a sufficient time to produce a hydrolysate of submucosa components. Typically the submucosa is treated with one enzyme, however the submucosa can be treated with a mixture of enzymes to hydrolyze the structural components of the submucosa and prepare a hydrolysate having multiple hydrolyzed submucosa components of reduced molecular weight. The length of digestion time is varied depending on the application, and the digestion can be extended to completely solubilize the submucosa. More preferably the submucosal tissue is partially solubilized to produce a submucosa digest composition comprising hydrolyzed submucosa components and nonhydrolyzed submucosa components.

In one embodiment the digest composition is further manipulated to remove at least some of the nonhydrolyzed components of the submucosa. For example, the nonhydrolyzed components can be separated from the hydrolyzed portions by centrifugation. Alternatively, other separation techniques familiar to those skilled in the art, such as filtration, can be used in accordance with this invention. Accordingly, partially solubilized submucosa can be filtered or subject to centrifugation to remove insoluble portions of the digest composition and thus form a substantially uniform hydrolysate of submucosal tissue. Removal of undigested submucosa from the hydrolysate does alter the composition of the hydrolysate but does not significantly alter the hydrolysate's ability to form a shape retaining gel.

The conditions used in the digestion of the submucosa produce a hydrolysate having an ionic strength that is not optimal for forming a shape retaining gel. The appropriate ionic strength can be obtained by fractionation of hydrolysate, however, the production of a shape retaining gel from submucosa hydrolysate species is believed to require that those species remain in solution during the fractionation step. Fractionation of the submucosa hydrolysate at physiological pH and physiological ionic strength reduces collagen solubility in the hydrolysate resulting in formation of a weak/non-shape retaining gel. Accordingly, the shape retaining gels of the present invention are prepared from enzymatically digested vertebrate submucosa that has been fractionated under acidic conditions (pH ranging from about 2.0 to less than 7.0). Typically, the submucosa hydrolysate is fractionated by dialysis against a solution having a pH ranging from about 2.0 to about 5.0. In one embodiment, the submucosa hydrolysate is fractionated under mild acidic conditions, wherein "mild acidic conditions" is defined as a pH ranging from greater than 3.0 to less than 7.0. In this embodiment, the submucosa hydrolysate is typically fractionated under mild conditions by dialysis against a solution having a pH ranging from greater than 3.0 to about 5.0. In addition to fractionating the hydrolysate under acidic conditions, the submucosa hydrolysate is typically fractionated under conditions of low ionic strength with minimal concentrations of salts such as those usually found in standard buffers such as PBS (i.e. NaCl, KCl, $Na_2HPO_4$, or $KH_2PO_4$). Such fractionation conditions work to reduce the ionic strength of the submucosa hydrolysate and thereby provide enhanced gel forming characteristics. In sum, the formation of the shape retaining gels of the present invention is optimized by fractionating the submucosa hydrolysate under acidic conditions and relatively low ionic strength.

The hydrolysate solution produced by enzymatic digestion of the submucosa has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested submucosal tissue. In accordance with the present invention the submucosa hydrolysate is fractionated under acidic and low ionic strength conditions to remove at least some of the original hydrolysate components. This step produces a fractionated submucosa hydrolysate that has an altered protein to carbohydrate ratio relative to the protein to carbohydrate ratio of the original delaminated submucosa. For example, digestion of vertebrate submucosa with a protease such as pepsin, followed by dialysis will form a fractionated submucosa hydrolysate having a lower protein to carbohydrate ratio relative to the original delaminated submucosa.

In accordance with one embodiment, a shape retaining gel form of submucosa is prepared from delaminated submucosa (having a predetermined protein to carbohydrate ratio) that has been enzymatically digested and fractionated under acidic conditions to form a submucosa hydrolysate that has a protein to carbohydrate ratio different than that of the original delaminated submucosa. In accordance with one embodiment, the submucosa hydrolysate (with or without the nonhydrolyzed submucosa portion) is fractionated by dialysis. The molecular weight cut off of the submucosa components to be included in the gel is selected based on the desired properties of the gel. Typically the pore size will range from about 3,500 to about 10,000, and more preferably from about 3,500 to about 5,000. The hydrolysate is dialyzed against an acidic solution having low ionic strength. For example, the hydrolysate can be dialyzed against a 0.01 M acetic acid (pH of approximately 3.3–3.5). In addition, the submucosa hydrolysate can be optionally sterilized during dialysis by the inclusion of chloroform in the dialysis buffer.

Vertebrate submucosa can be stored frozen (at about –20 to about –80° C.) in either its solid, comminuted or enzymatically digested forms prior to formation of the gel compositions of the present invention or the material can be stored after being hydrolyzed and fractionated. Storage temperatures are selected to stabilize matrix components and typically the fractionated submucosa hydrolysate is stored at 4° C. for about a week, but it can be stored at 0–4° C. for 1–26 weeks, or for longer, if the storage temperature is less than 0° C. Submucosa is stored in solvents that maintain the collagen in its native form and solubility. For example, one suitable storage solvent is 0.01 M acetic acid, however other acids can be substituted, such as 0.01 N HCl. In accordance with one embodiment the fractionated submucosa hydrolysate is dried (by lyophilization, for example) and stored in a dehydrated/lyophilized state. The dried form can be rehydrated and gelled to form the shape retaining gel of the present invention.

In accordance with one embodiment, the fractionated submucosa hydrolysate is gelled by adjusting the pH to about 5.0 to about 9.0, more preferably about 6.6 to about 7.4 and typically about 7.0 to about 7.2 thus inducing fibrillogenesis and matrix gel assembly. In one embodiment the pH of the fractionated hydrolysate is adjusted by the addition of a buffer that does not leave a toxic residue, and has a physiological ion concentration and the capacity to hold physiological pH. Examples of suitable buffers include PBS, HEPES, and DMEM. In one embodiment the pH of the fractionated submucosa hydrolysate is first raised to greater than 8.0 by the addition of a base, such as NaOH and then lowered to about 6.0 to about 8.0, more preferably about 6.6 to about 7.4 by the addition of an acid, such as HCl. In accordance with one embodiment, the submucosa hydrolysate is mixed with 10×PBS Buffer in an 8:1.2 ratio and sufficient 0.05 N NaOH is added to shift the pH to >8. Then sufficient 0.04 N HCl is added to adjust the pH to between 6.6 and 7.4. The resultant mixture is aliquoted into designated cultureware or appropriate forms and incubated at 37° C. for 0.5 to 1.5 hours. The present submucosal gel compositions can be combined with added growth factors, therapeutics, cells, etc., for specific applications (e.g., vehicle for cell delivery, delivery of drugs/therapeutics, 3-dimensional cell culture substrate, and augmentation of tissue repair). The ionic strength of the submucosa hydrolysate is believed to be important in maintaining the fibers of collagen in a state that allows for fibrillogenesis and matrix gel assembly upon neutralization of the hydrolysate. Accordingly, it may be important to reduce the salt concentration of the submucosa enzyme digest prior to neutralization of the hydrolysate.

After the pH of the fractionated submucosa hydrolysate has been adjusted to about 6.0 to about 8.0, more preferably about 6.6 to about 7.4, the solution can be placed in the appropriately shaped container for forming a shaped gel. For example, the solution can be poured onto cell cultureware to conform to the shape of the cultureware before the gel sets. Typically the neutralized, fractionated, hydrolysate is incubated at 37° C. to form the gel. The neutralized hydrolysate gels in approximately thirty to ninety minutes at 37° C. Alternatively, the gel can be stored at 4° C. to delay the setting of the gel for 3–8 hours. The neutralized hydrolysate can be gelled at any temperature ranging from about 4° C. to about 40° C. Gellation times range from 5 to 120 minutes at the higher gellation temperatures and 1 to 8 hours at the lower gellation temperature. Additional components can be added to the hydrolysate composition before gellation of the composition. For example, proteins carbohydrates, growth factors, bioactive agents, nucleic acids or pharmaceuticals can be added.

The shape retaining gels of the present invention are translucent, having an optical density ranging from about 0.1 to about 2.0 at A405 nm, more preferably from about 0.4 to about 1.2 at A405 nm and more typically about 0.6 to about 0.8 A405 nm. Dialysis of the submucosa hydrolysate against various ionic solutions impacts the turbidity and firmness of the formed gel. The turbidity and firmness of the gel increase relative to the ionic composition of the dialysis solution (PBS<HCl≦Acetic Acid) and is correlated with the matrix component solubility as indicated by a lower initial optical density. Dialysis using a PBS dialysis solution only produced weak gels, whereas dialysis against an acetic acid or HCl solution produces a shape retaining gel having a turbidity of less than 1.2 at A405 nm. After formation of the shape retaining gel, the matrix can be dried/dehydrated and stored. The gel can be subsequently dehydrated without loss of its bioactive properties.

In accordance with one embodiment of the present invention a shape retaining gel matrix is prepared from vertebrate submucosa by enzymatically treating warm-blooded vertebrate submucosa to produce a hydrolysate of warm-blooded vertebrate submucosa. The submucosa hydrolysate is then fractionated to reduce the concentration of hydrolysate components having a molecular weight less than 3500, and the remain fractionated submucosa is gelled by adjusting the pH to about 5.0 to about 9.0, more preferably by adjusting the pH to about 6.0 to about 8.0. In accordance with one embodiment the pH of the fractionated submucosa is adjusted to greater than 8.0 before adjusting the pH to about 6.0 to about 8.0. The method also includes, in one embodiment, the step of separating at least some of the undigested and insoluble components of the submucosa hydrolysate from the solubilized components. One preferred method for removing the nonhydrolyzed components comprises centrifuging the submucosa hydrolysate and recovering the supernatant. Alternatively, the submucosa hydrolysate can be filtered to remove the insoluble submucosa hydrolysate components. The hydrolysate is fractionated to remove at least some of the low molecular weight submucosa hydrolysate species, and typically this step is accomplished by dialyzing against an acidic solution. The pH of the fractionated submucosa hydrolysate is then adjusted to about 6.0 to about 8.0 and the fractionated submucosa hydrolysate is incubated the at 37° C. to form the shape retaining gel.

In accordance with one embodiment, a gellable composition is prepared by grinding vertebrate submucosa into a powder and partially digesting the powdered submucosa with 0.1% pepsin in 0.5 M acetic acid for one to two days at 4° C. Following partial digestion, the hydrolyzed submucosa is separated from the undigested portions by centrifuging the suspension at 4° C. to pellet the undigested material. The supernatant, comprising solubilized submucosa is recovered and the insoluble pellet discarded. The supernatant is then fractionated to remove at least a portion of the hydrolysate components. In one embodiment, the hydrolysate is fractionated by dialyzing the hydrolysate under mild acidic conditions and low salt (i.e., salt concentration lower than physiological salt concentrations). In one embodiment the hydrolysate is dialyzed against several changes of 0.01 M acetic acid at 4° C. using dialysis membranes having a molecular weight cut off of 3500. Therefore, in this embodiment the hydrolysate is fractionated to remove the hydrolysate components having a molecular weight of less than 3500. Alternatively, different pore sized dialysis tubing can be used to alter the composition of the submucosa gel formed in accordance with the present invention.

In one embodiment the submucosa is sterilized before formation of the gel, however the submucosa can also be sterilized after the formation of the gel matrix. In one embodiment the submucosa hydrolysate is sterilized during the dialysis step. For example, chloroform (5 ml chloroform per 900 ml of 0.01 M acetic acid) can be added to the dialysis solution to disinfect or sterilize the submucosa. Typically when the submucosa hydrolysate is sterilized by dialysis against chloroform, two additional changes of sterile 0.01 M acetic acid are used to eliminate the chloroform.

In general, isolated vertebrate submucosa can be sterilized using conventional sterilization techniques including glutaraldehyde tanning, formaldehyde tanning at acidic pH, propylene oxide treatment, gas plasma sterilization, gamma radiation, electron beam, peracetic acid sterilization. Sterilization techniques which do not adversely affect the mechanical strength, structure, and biotropic properties of the submucosal tissue is preferred. Preferred sterilization techniques include exposing the submucosa to 1–4 Mrads gamma irradiation (more preferably 1–2.5 Mrads of gamma irradiation) or gas plasma sterilization. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

In accordance with one embodiment a method for inducing the growth of cells in vivo, is provided. The method comprising the step of injecting into a host at a site in need of repair a composition comprising enzymatically digested vertebrate submucosa that is fractionated to reduce the concentration of enzymatically digested vertebrate submucosa components having a molecular weight less than 3500. In one embodiment the fractionated submucosa hydrolysate is neutralized (for example, by adding a physiologically compatible buffer) before injection, and the hydrolysate is injected into the host before the gel matrix sets. The injected material then gels at the in vivo site of injection thus immobilizing the composition at the injection site. The resulting shape retaining gel stimulates endogenous cell proliferation and cell growth/function at the localized injection site and enhances the repair of damaged or diseased tissues. Advantageously this technique allows for the fixation of a matrix composition at a localized site through a minimally invasive procedure. The fractionated hydrolysate can be combined with added growth factors, pharmaceuticals, minerals, bioactive agents or cells prior to injection and formation of the gel matrix.

Alternatively, in one embodiment a shape retaining gel for inducing cell growth in vivo is prepared, comprising a fractionated submucosa hydrolysate in combination with added components. This composition is formed by enzymatically digesting vertebrate submucosa to form a submucosa hydrolysate, and then fractionating the hydrolysate and neutralizing the fractionated hydrolysate to form a shape retaining gel. The additional components are added to the fractionated hydrolysate either before the neutralization step or immediately after the neutralization step and before the gel sets. The mixture is then stirred and allowed to form a shape retaining gel of a predetermined shape. In one embodiment the gel is formed to match the shape of an implantation site in a host and the formed gel is surgically implanted into the host at that site. Various components can be added to the submucosa hydrolysate to form gel matrix compositions in accordance with the present invention, including, but not limited to, proteins, carbohydrates, growth factors, bioactive agents, minerals pharmaceuticals and cells.

The shape retaining gel matrix forms of the present invention can be used as cell culture substrates for supporting the attachment, growth or proliferation of a wide variety of cell types in vitro. The gel matrix comprises a submucosa hydrolysate fraction having multiple hydrolyzed submucosa components, wherein the hydrolysate fraction is prepared from enzymatically digested vertebrate submucosa fractionated to reduce the concentration of hydrolysate components having a molecular weight less than about 3500. The composition is gelled by adjusting the pH to about 6.0 to about 8.0. The gelled forms of submucosal tissue provide a translucent substrate for cell adhesion and also induce cell differentiation. The submucosal tissue is preferably sterilized prior to use in cell culture applications, however nonsterile submucosal tissue can be used if antibiotics are included in the cell culture system. In one embodiment the gelled submucosal tissue is used to coat cultureware (i.e. petri plates, culture bottles or flasks, etc.,) and is used in combination with standard liquid culture media. To prepare gelled submucosa coated cultureware, the fluidized form of submucosal tissue can be poured onto the cultureware and gelled by adjusting the pH of the submucosa tissue to about 6.0 to 8.0.

In accordance with one embodiment a submucosa gel composition is prepared for use in culturing cells in vitro. In one embodiment the composition comprises tissue cultureware that is coated with a composition comprising intestinal submucosa delaminated from both the tunica muscularis and at least the luminal portion of the tunica mucosa, wherein the delaminated submucosa is enzymatically treated, fractionated under acidic conditions to alter the protein to carbohydrate ratio of the original delaminated submucosal tissue, and then gelled. In preferred embodiments the fractionated submucosa hydrolysate is gelled by adjusting the pH of the hydrolysate to about 6.0 to about 7.4. In another embodiment of the present invention, a composition for culturing cells in vitro, comprises tissue cultureware coated with a shape retaining gel matrix comprising an enzyme hydrolysate of warm-blooded vertebrate submucosa that was fractionated to remove at least a portion of the hydrolysate components having a molecular weight less than 3,500, and gelled by adjusting the pH to about 6.0 to about 7.4.

The cell growth substrate of the present invention can be combined with added agents, including minerals, amino acids, sugars, peptides, proteins, glycoproteins, proteoglycans, cytokines, growth factors, drugs, plasmids, vectors, or other bioactive agents that facilitate or inhibit cellular proliferation or differentiation. Other examples of such agents include laminin, fibronectin, epidermal growth factor, platelet-derived growth factor, transforming growth factor beta and fibroblast growth factor. The submucosa substrates of the present invention can be used with commercially available cell culture liquid media (both serum based and serum free). When grown in accordance with this invention, proliferating cells can either be in direct contact with the submucosa or they can simply be in fluid communication with the gelled submucosa. It is anticipated that the cell growth compositions of the present invention can be used to stimulate proliferation of undifferentiated stems cells as well as differentiated cells such as islets of Langerhans, hepatocytes and chondrocytes. Furthermore the described cell growth composition is believed to support the growth of differentiated cells while maintaining the differentiated state of such cells.

EXAMPLE 1

Preparation of Shape Retaining Gel Matrices

Small intestinal submucosa was harvested and prepared from freshly euthanized pigs (Delphi Indiana) as previously disclosed in U.S. Pat. Nos. 4,902,508 and 4,956,178. Intestinal submucosa was powderized under liquid nitrogen and stored at −80° C. prior to use. Partial digestion of the material was performed by adding 5 g powdered tissue to each 100 ml solution containing 0.1% pepsin in 0.5 M acetic acid and digesting for 72 hours at 4° C. Following partial digestion, the suspension is centrifuged at 12,000 rpm for 20 minutes at 4° C. and the insoluble pellet discarded. The supernatant was dialyzed against several changes of 0.01 M acetic acid at 4° C. (MWCO 3500). The solution was sterilized by adding chloroform (5 ml chloroform to each 900 ml 0.01 M acetic acid) to the dialysis submucosal tissue reservoir. Dialysis of the submucosal tissue was continued with two additional changes of sterile 0.01 M acetic acid to eliminate the chloroform. The contents of the dialysis bag were then transferred aseptically to a sterile container. The resultant solution may be stored at 4° C. To prepare the gel form of the intestinal submucosa, 8 mls of intestinal submucosa solution was mixed with 1.2 ml 10×PBS Buffer (10×phosphate buffered saline containing 5 mg/L phenol red); 0.05 N NaOH (approx. 1.2 ml) was added to shift the pH to >8 and then 0.04 N HCl (approx 1.6 ml) was added to adjust the pH to between 6.6 and 7.4. The final volume was adjusted to 12 ml with water. The resultant mixture was then aliquoted into designated cultureware or appropriate forms and incubated at 37° C. for 0.5 to 1.5 hours.

EXAMPLE 2

Use of the Shape Retaining Gel Matrix as a Cell Culture Substrate

MATERIALS AND METHODS

Cell Culture:

Swiss mouse 3T3 fibroblasts were obtained from American Type Culture Collection (ATCC), Rockville, Md. Primary human urinary bladder stromal cells (HUBS) were derived from bladders of patients undergoing ureteral reimplantation for vesicoureteral reflux and were generously provided by Dr. E. Cheng, Northwestern University, Chicago, Ill. Primary canine prostate carcinoma cells; were established from a primary tumor of a dog with prostate adenocarcinoma and were kindly provided by Dr. D. Waters, Purdue University, West Lafayette, Ind. Rat pulmonary endothelial cells were isolated from rat pulmonary arteries, purified by flow cytometric fluorescence-activated cell sorting. The cell types, source information, and medium conditions involved in these experiments are summarized in Table 1.

TABLE 1

| NAME | ORIGIN/SOURCE | MEDIUM |
|---|---|---|
| 3T3 | Swiss Mouse Embryo Fibroblasts; American Type Culture Collection, CRL 1658 | DMEM (Dulbecco's modified Eagle's medium) with 1.5 g/L NaHCO$_3$, 10% NNCS (neonatal calf serum), 100 U/ml penicillin, 100, µg/ml streptomycin, 2 mM L-glutamine |
| RPEC | Rat Pulmonary Artery Endothelial Cells; J. P. Robinson, Purdue University | RPMI 1640, 5% NCS (newborn calf serum), 5% FBS (fetal bovine serum), 100 U/ml penicillin, 100 µg/ml streptomycin, 2 mM L-glutamine |
| HUBS | Human Urinary Bladder Stromal Cells; E. Cheng, Northwestern University | Modified medium 199 supplemented with 10% NCS (newborn calf serum), 2.5 µg/ml fungizone and 50 µg/ml gentamicin (Baskin et al, 1993); medium modifications included the addition of sodium bicarbonate (2.2 g/L), bactopeptone (0.5 g/L), glucose (3.0 g/L), L-glutaine (0.29 g/L), HEPES (3.57 g/L), 100X BME vitamins (10 ml/L, Flow Labs), and 100X BME amino acids (10 ml/L, Gibco, Grand Island, New York) |
| Clemons | Canine Prostate Adenocarcinoma; D. Waters, Purdue University | RPMI 1640, 10% FBS, 100 U/ml penicillin, 100 µg/ml streptomycin, 2 mM L-glutamine |

Substrata:

Vitrogen and Matrigel were obtained from Collagen Corporation (Fremont, Calif.) and Collaborative Biomedical (Bedford, Mass.), respectively. All tissue culture plastics were obtained from Coming Inc. (Coming, N.Y.).

Preparation of Intact Submucosal Tissue and Submucosal Tissue-Derived Gel.

Intestinal submucosa was prepared from the small intestines of market weight pigs obtained from a local meat processing plant. In brief, intestine was rinsed free of contents, everted, and the superficial layers of the mucosa were removed by mechanical delamination. The tissue was reverted to its original orientation and the external muscle layer removed. The prepared intestinal mucosa tube was split open longitudinally and rinsed extensively in water to lyse any cells associated with the matrix and to eliminate cell degradation products. Immediately, after rinsing, the intestinal submucosa was disinfected with 0.1% peracetic acid for cell culture or frozen in liquid nitrogen and stored at $-80°$ C. for preparation of submucosal tissue-derived gel forms.

For preparation of submucosal tissue-derived gel forms, frozen tissue first was pulverized under liquid nitrogen with an industrial blender and stored at $-80°$ C. prior to use. Submucosal tissue powder (5% w/v) was suspended in 0.5 M acetic acid containing 0.1% pepsin and vigorously stirred for 72 hours at $4°$ C. The mixture then was centrifuged at 12,000 rpm for 20 minutes at $4°$ C. to remove undigested tissue. The supernatant was dialyzed extensively against 0.01 M acetic acid at $4°$ C. in spectrapor tubing (MWCO 3500, Spectrum Medical Industries). To obtain a sterile preparation, the solution was dialyzed against 0.01 M acetic acid containing chloroform (approx. 0.5% v/v), followed by several changes of sterile 0.01 M acetic acid. To induce fibrilogenesis in the fractionated submucosal tissue hydrolysate, 1.2 ml 10×PBS (1.37 M NaCl, 26.8 mM KCl, 0.1 M $Na_2HPO_4$, and 17.6 mM $KH_2PO_4$, and 5 mg/L phenol red, pH 7.4) and 1.2 ml 0.1 NaOH were added to 8 ml of submucosal tissue extract. This solution was brought to pH 7 with 0.1 M HCl, aliquotted into 24-well plates, and incubated at $37°$ C. for 30–60 minutes to form a gel.

Scanning Electron Microscopy:

Substrata were fixed in 3% glutaraldehyde in Millonig's buffer and post fixed in 1% osmium, tetroxide. Fixed specimens were dehydrated in a graded series of acetones, critical point dried, affixed to scanning stubs, and sputter coated with gold/palladium. Specimens were viewed with a JEOL JSM-840 scanning electron microscope. Gelled substrata also were quick frozen by plunging into a liquid nitrogen slush without prior fixation or dehydration. The sample was transferred into a CT1000 coldstage attachment (Oxford Instruments North America, Inc., Concord, Mass.) and the surface was fractured and coated with gold prior to viewing at temperatures of $-150°$ C. with the SEM.

Cell Growth on Substrata:

Twenty-four-well tissue culture plates were prepared with Matrigel (500 μl/well), Vitrogen (500 μl/well), submucosal tissue, submucosal tissue-derived gel (500 μl/well), or no substrate. Submucosal tissue material was affixed in polypropylene frames with the mucosal surface facing upward to create a well area of 0.5 $cm^2$. All substrata, were equilibrated with sterile PBS, pH 7.4 prior to the application of cells.

Cells were harvested in complete medium (refer to Table 1) and seeded upon substrata at 60,000 cells/$cm^2$. For certain experiments, cells were labeled with the fluorescent cell membrane dye PKM26 (Sigma, St. Louis, Mo.) prior to seeding upon the substrata. Culture plates were incubated at $37°$ C. in a humidified atmosphere of 5% $CO_2$ in air and fed 2–3 times weekly. On days 1, 4, 7, and 14, the cells and associated substrate (intact submucosal tissue only) were fixed and processed for light or fluorescence microscopy.

Fluorescence Microscopy.

Cells labeled with fluorescent markers were fixed in 4% paraformaldehyde and observed using a fluorescence microscope (Labophot, Nikon).

Light Microscopy:

Cell growth on plastic, Matrigel, Vitrogen, and submucosal tissue-derived gel was observed daily using a standard inverted microscope. Digital images were collected on days 1, 4, 7, 11, and 14 using an inverted microscope, video camera (Sanyo, Japan), and Digital Video Producer software (Asymetrix) on a 755CD laptop computer (IBM).

Histology

Cells and associated substratum were fixed in neutral buffered formalin, embedded in paraffin, sectioned to 6 μm, and stained with hematoxylin and eosin (H&E). Morphological evaluation was conducted using light microscopy.

Results

Morphological Appearance and Characterization

It has been well documented that physical, geometrical, and topological features of substrata affect cell behavior both in vitro and in vivo. Therefore, architectural features of submucosal tissue, submucosal tissue-derived gel, Vitrogen and Matrigel were determined and subsequently compared. Small intestine represents a multilayered organ consisting of mucosa, lamina propria, muscularis mucosa, submucosa, muscularis external and serosa. Preparation of submucosal tissue involved mechanical removal of the outermost epithelial and muscle layers and the removal to the luminal portion of the tunica mucosa. Treatment of the remaining submucosa, muscularis mucosa and remnant lamina propria layers under hypotonic conditions provided an acellular ECM designated submucosal tissue.

Initial structural analysis was performed using routine critical point drying of specimens followed by scanning electron microscopy (SEM). Low magnification SEM demonstrated the disparity in the topography of the mucosal and serosal surfaces of intact submucosal tissue. The relatively smooth mucosal surface which once supported the epithelial lining of the intestine showed multiple folds and involutions. Whereas, the fibrillar nature of the serosal side was evidenced by its more ragged appearance. Ultrastructurally, the mucosal surface was characterized by more densely packed fibers that form discontinuous layers varying in orientation. Alternatively, the serosal side exhibited a fine network of loosely organized fibers, most of which are <1 μm in diameter. Although most fibers appeared to be organized randomly, some formed assemblies to create larger fibers.

Analysis of submucosal tissue-derived matrices and Vitrogen prepared using critical point drying techniques demonstrated a tightly woven network of small diameter fibrils with extensive lateral association. Matrigel, on the other hand featured a more densely compact, sheet-like surface. Although some appreciation of substrate architecture was obtained from critical point dried specimens, excessive shrinkage was noted. To minimize the possibility of structural artifacts induced by such preparatory techniques, quick freeze, cold stage SEM was employed. This technique obviated the need for both chemical fixation and dehydration. Results obtained using this method more accurately represent the detailed macromolecular structure of samples with high water content. With cold stage SEM, the marked differences in the ultrastructure of the three substrata, were obvious. Submucosal tissue-derived gel consisted of a network of loosely organized fibrils that varied in size. The fine fibers composing Vitrogen appeared more randomly oriented and formed regions of dense aggregates with extensive cross-branching. Matrigel featured a honeycomb lattice with very fine, cobweb-like fibers decorating the individual honeycomb cells.

Effect of Substratum on Cellular Behavior and Morphology

The submucosal tissue matrix provided a ready source of ECM, and its mucosal surface supported distinct morphological responses of the four different cell types studied—fibroblasts (Swiss mouse 3T3), endothelium (rat pulmonary artery), glandular epithelium (canine prostate adenocarcinoma), and smooth muscle-like cells (human urinary bladder stromal). In all cases, specific cell-submucosal tissue interactions more closely approximated those which are observed in vivo, especially when compared to plastic, Matrigel, and Vitrogen.

Fibroblasts:

Swiss 3T3 fibroblasts, when grown on plastic, readily proliferated and exhibited a spindle shaped morphology at subconfluence. At confluence, which was achieved within 4 days, these cells demonstrated contact inhibition and appeared more cuboidal in shape. Swiss 3T3 Fibroblasts responded in a similar fashion when cultured on Vitrogen. After 4 days, the cells had formed a confluent monolayer of cuboidal shaped cells along the substrate surface. The presence of a few spindly-elongated shaped cells in focal planes below the surface suggested penetration of a limited number of individual cells into the collagen matrix. The same cells showed a dramatically different response when grown on Matrigel. Within 24 hours, fibroblasts appeared spindle-shaped but formed regional aggregates. These aggregates persisted throughout the 14-day timecourse with no obvious proliferative activity. When cultured on submucosal tissue-derived gel, fibroblasts maintained a spindly-elongated shape throughout the 14 day observation period. The ability of fibroblasts to proliferate and more readily penetrate the submucosal tissue-derived gel was evidenced by numerous fibroblasts in multiple focal planes along and within the matrix. Intimate cell-cell contact was not apparent; however, the cells within a single focal plane did show parallel alignment.

The invasion and morphological characteristics of fibroblasts on submucosal tissue-derived gel resembled those observed in vivo. Similar in vivo-like behavior was observed by fibroblasts seeded on the mucosal side of intact submucosal tissue. The cells were fusiform to spindly in shape and actively proliferated and migrated into the tortuous fiber network of the small intestinal matrix. The fibroblasts appeared as individual cells compressed among the collagenous fibers suggesting active cell-ECM as well as cell-cell interaction. Taken together, the 3D growth pattern and behavior of fibroblasts as well as the natural ECM architecture inherent to submucosal tissue was reminiscent of connective tissue in vivo.

Endothelium:

A homogeneous population of endothelial cells was derived from rat pulmonary arteries followed by fluorescence-activated cell sorting using flow cytometry. On plastic, these cell displayed the traditional "cobblestone" morphology, characteristic of most macrovascular endothelial cells. A different morphological pattern was exhibited by these endothelial cells when grown on Vitrogen and submucosal tissue-derived gel; endothelial cells cultured on either substrata appeared spindle to stellate shaped with multiple cytoplasmic projections. By day 7 the cells proliferated to form confluent monolayers of spindly to round shaped cells. Little to no penetration of cells into either Vitrogen or submucosal tissue-derived gel was observed. As with fibroblasts, endothelial cells showed a distinct response to Matrigel. A rapid aggregation of cells was observed within 24 hours. Interestingly, some aggregates were connected by long canalicular-like processes, which regressed by 72 hours. While endothelial cells readily and rapidly proliferated on plastic, Vitrogen and submucosal tissue-derived gel substrates; no significant increase in cell number was observed on Matrigel. On submucosal tissue, rat pulmonary endothelial cells grew primarily along the surface of the substrate as cuboidal shaped cells creating a "cobblestone" pattern. At early timepoints cell-cell interaction predominated such that the cells formed a cellular layer 1–2 cells thick, reminiscent of the endothelial layer common to blood vessels. At later timepoints, endothelial cells were seen to penetrate the matrix and in some cases formed a new endothelial lining along preexisting vessel tunnels.

Glandular Epithelium:

The canine prostate carcinoma cell line, Clemons, used in this study was originally isolated from a primary tumor and propagated in culture. Immunohistochemical staining confirmed the presence of cytokeratin, an intracellular marker characteristic of the epithelial cell phenotype. During the first 24 hours of culture, Clemons cells attached and appeared morphologically similar on plastic, Vitrogen, and submucosal tissue-derived gel. On all three substrata, the cells grew initially as flattened cells, most of which coalesced to form heterogeneous shaped patterns. After 4 days in culture, subtle differences were observed in the cellular response to submucosal tissue-derived gel compared to the other two substrata. On Vitrogen and plastic, the cells continued to grow along the substrate surface as a single layer of flattened cells. In contrast, submucosal tissue-derived gel induced regional piling of cells into multilayered aggregates. Cells reached confluence between days 7 and 11 on plastic, Vitrogen, and submucosal tissue-derived gel. However, even at confluence, cells on plastic maintained a 2D growth pattern. While some evidence of multilayer cell aggregation was noted on Vitrogen, the most extensive 3D pattern was developed by cells on submucosal tissue-derived gel. When grown on Matrigel, Clemons cells attached and formed aggregates within 24 hours. In some cases the aggregates were connected by long canalicular-like processes. At later timepoints, the interconnecting structures receded leaving dense aggregates scattered along the surface. On Matrigel, no significant increase in cell number was noted at any timepoint up to 14 days.

Unlike Matrigel, intact submucosal tissue induced attachment, proliferation, and polarization of Clemons cells in vitro Initially, cells grew as aggregates 1–3 cells thick along the surface of the submucosal tissue. By day 7 a confluent layer of cells covered the surface of submucosal tissue with some organized areas resembling early follicle formation. By day 14, numerous structures composed of epithelial cells organized around a central lumen were evident, reminiscent of acini. Although these cells grew primarily along the surface of submucosal tissue, in some sections, isolated foci of cells were identified within the matrix.

Smooth Muscle-Like Cells:

Primary cultures of stromal cells were derived from human urinary bladders and subsequently propagated in vitro. Immunohistochemical staining confirmed the presence of vimentin, smooth muscle α-actin and smooth muscle myosin, characteristic of the smooth muscle phenotype. When grown on plastic, stromal cells displayed a characteristic spindle-shaped morphology with a centrally located round to oval nucleus. At early timepoints, up to 4 days, this morphology was observed of stromal cells on Vitrogen and submucosal tissue-derived gel. However, as the cells continued to proliferate on the different substrata, distinct morphologies developed. Stromal cells formed aggregated ridges of cells that were grossly and microscopically visible on plastic and Vitrogen as early as 4 days and 7 days, respectively. In contrast, stromal cells grown on submucosal tissue-derived gel readily proliferated and penetrated into the matrix to form multiple layers of aligned cells. No ridge formation was observed on the submucosal tissue substrata at any timepoint investigated. Matrigel induced a significantly different response characterized by regional aggregates of cells. This morphology was observed within the first 24 hours of incubation and persisted with no obvious proliferative activity by the cells up to 14 days. The ability of submucosal tissue to induce tissue-specific histogenesis was also observed with stromal cells. On submucosal tissue, the stromal cells maintained their spindle shape with a centrally-located, prominent nucleus. Within 7 days, the cells proliferated and migrated throughout the matrix. organizing into thick bands or multilayers of parallel aligned cells.

Discussion

To date the majority of cell culture experimentation has been performed in a 2-dimensional format on artificial (synthetic) substrata consisting of glass or plastic. While polystyrene is by far the most commonly used artificial substrate, cells have also been successfully grown on polyvinylchlorinade (PVC), polycarbonate, polytetrafluoroethylene (PTFE), melinex, and thermanox (TPX). Because of their attractiveness for tissue engineering applications, a number of bioabsorbable synthetic polymers have been investigated for the culture and delivery of cells. These include polyglycolic acid, poly L-lactic acid, and polyglycolic-co-lactic acid. Although the chemical and physical properties of these substrata can be controlled, these materials lack the ability of ECM to predictably signal (orchestrate) fundamental cellular processes. Therefore, when cells are isolated from their natural ECM, cultured, and propagated under these conditions, the resultant cell phenotype is often different from that observed in the tissue from which it was derived.

As observed with the majority of vertebrate cells, fibroblastic (Swiss mouse 3T3), endothelial (rat pulmonary artery), glandular epithelial (canine prostate adenocarcinoma), and smooth muscle-like (human bladder stromal) cells used in this study were limited to simple 2D morphological patterns when grown on plastic. It is said that continuous exposure of cells to plastic often results in loss of morphology as well as biochemical and functional properties, a process referred to as dedifferentiation. The fact that many molecules of the extracellular matrix exhibit the ability to self-assemble into highly ordered arrays has allowed the development of two routinely used 3D substrata, Matrigel and Vitrogen. Vitrogen represents a more simplified substrate in that it is composed of Type I collagen purified from bovine dermis. Structurally, Vitrogen represents an irregular arrangement of dense fibrillar aggregates laced with a network of thin fibrils. Matrigel, on the other hand, is an extract of basement membrane secreted by Engelbreth Holm Swarm tumor cells in vitro, the physiologic relevance of which is uncertain. That matrix consists of collagen IV, laminin, and heparan sulfate proteoglycan along with several growth factors. Matrigel forms a honeycomb structure along the interwoven fibrils of type IV collagen.

The ability of submucosal tissue and submucosal tissue-derived gel to serve as a cell culture scaffold was demonstrated by the ability of all four cell types studied to attach, survive, proliferate, and in some cases differentiate on these matrices. Interestingly, each cell type was distinct in its behavior and appearance when cultured on submucosal tissue and submucosal tissue-derived gel. Moreover, the importance of substrate architecture and composition on cell behavior in vitro was apparent by the disparity in morphologic patterns developed by each cell type on the 3D substrata evaluated. For instance, long term culture (up to 14 days) of RPEC or Clemons on Vitrogen, submucosal tissue-derived gel and submucosal tissue resulted in relatively similar morphologies. On the other hand, patterns developed by 3T3 fibroblasts and bladder stromal cells on submucosal tissue and submucosal tissue-derived gel were distinct from those observed on the other substrata evaluated. All four cell types responded in a dramatically different fashion when cultured on Matrigel. Matrigel promoted rapid cell-cell interaction with formation of aggregates within 24 hours of seeding. This rapid aggregation was accompanied by a loss of proliferative activity, a response documented previously by a number of other cell types including rat capillary endothelial cells, bovine retinal pigmented epithelial and lens cells, mouse Leydig cells, and normal and tumor-derived primary human mammary epithelial cells.

3T3 fibroblasts attached and proliferated but showed no penetration into the type I collagenous network of Vitrogen. In addition, Vitrogen induced formation of a monolayer of cuboidal shaped cells, a pattern similar to that developed by fibroblasts on plastic. These findings are in agreement with studies performed by Elsdale and Bard (J. Cell Biol. 54, 626 (1972)) involving human fibroblasts and type I collagen derived from rat tail tendon. In contrast, intact and gelled forms of submucosal tissue fostered more cell-substrate interaction as evidence by the fusiform shape and intimate integration of fibroblasts within matrix components. Such behavior and histogenesis is common place of the fibroblast phenotype as it occurs naturally in connective tissue structures in vivo. In fact, it would be difficult to distinguish the histology generated by fibroblasts cultured on intact submucosal tissue in vitro from that of a naturally occurring connective tissues such as the dermis or submucosa layer of the intestine.

Previous investigations have shown that the composition of the extracellular matrix plays a significant role in influencing the behavior of endothelial cells in vitro. Endothelial cells are well known for their ability to form "cobblestone" morphology on plastic. However in 3D culture, a variety of responses have been observed depending upon cell source (e.g., macrovascular or microvascular) and the nature of the substrata. In the present study, macrovascular RPEC cells formed a layer 1–3 cells thick across the surface of Vitrogen, submucosal tissue-derived gel and intact submucosal tissue. Although some penetration of these matrices was suspected, the majority of cells remained along the surface of the substrata. The morphological characteristics of RPEC cells to Matrigel observed in the present study are similar to those obtained with rat aorta and human umbilical vein endothelial cells. However, further investigations have shown that these morphological changes likely did not involve the typical transcriptional and translation events of endothelial cell differentiation.

The induction of polarization, stratification, and even acini formation by glandular epithelial cells in 3D culture systems is well documented. In fact, tissue specific phenotypic expression has been observed with both normal and tumorigenic epithelial cells including human mammary epithelial cells, rectal adenocarcinoma cells, and thyroid epithelial cells. The results of the present experiment demonstrate the ability of canine prostate adenocarcinoma cells to develop 3D morphological patterns when cultured on Vitrogen, Matrigel, submucosal tissue-derived gel and intact submucosal tissue but not on plastic. Interestingly, the rapid aggregation on Matrigel stabilized within 24–48 hours, with no obvious proliferation. In contrast, both proliferation and differentiation were noted on Vitrogen, submucosal tissue-derived gel and intact submucosal tissue. The acini formed resembled those which would be expressed by this cell type in vivo.

The culture of smooth muscle cells in vitro has routinely been difficult due to loss of expression of smooth muscle specific protein markers (e.g., $\alpha$-actin, myosin, caldesmon) along with contractile function. This is the first demonstration of the influence of different ECM substrata on the growth and behavior of human bladder stromal cells. The formation of multilayered arrays without contact inhibition of growth by fetal bovine and human bladder smooth muscle cells on plastic has been previously reported. Although a similar growth pattern was observed in the present experiment with short culture periods on plastic, Vitrogen, submucosal tissue-derived gel and intact submucosal tissue, long term persistence of this pattern (>14 days) occurred only on intact submucosal tissue and submucosal tissue-derived gel. Stromal cells not only penetrated the matrix but also formed bundles or arrays of parallel aligned cell characteristic of the stromal layer of urogenital tissues from which they were derived.

The ability of submucosal tissue to induce tissue-specific morphogenesis of cells was demonstrated initially in vivo and now in vitro. In summary, for the four cell types investigated, intact submucosal tissue and submucosal tissue-derived gel were equivalent or superior in their ability to support and maintain expression of tissue specific phenotype and behavior when compared to the routinely used 3D substrata Vitrogen and Matrigel.

The invention claimed is:

1. A method for inducing the growth of cells in vivo, comprising the steps of:
    forming a shape-retaining gel by fibrillogenesis of a submucosa tissue hydrolysate wherein the shape-retaining gel has an added bioactive component;
    then implanting said shape-retaining gel in a host to induce the growth of the cells in the host; and
    inducing the growth of cells in the host.

2. The method according to claim 1, wherein the added bioactive component is a protein.

3. The method according to claim 1, wherein the added bioactive component is a carbohydrate.

4. The method according to claim 1, wherein the added bioactive component is a growth factor.

5. The method according to claim 1, wherein the added bioactive component is a mineral.

6. The method according to claim 1, wherein the added bioactive component is a pharmaceutical.

* * * * *